United States Patent [19]

Chung et al.

[11] Patent Number: 5,314,898

[45] Date of Patent: May 24, 1994

[54] ARYL THIOPYRANO[4,3,2-CD]INDOLES AS INHIBITORS OF LEUKOTRIENE BIOSYNTHESIS

[75] Inventors: John Y. L. Chung, Edison; Robert A. Reamer, Bloomfield, both of N.J.; Yves Girard, Ile Bizard; Pierre Hamel, Vimont, both of Canada

[73] Assignees: Merck & Co., Inc., Rahway, N.J.; Merck Frosst Canada Inc., Kirkland, Canada

[21] Appl. No.: 906,062

[22] Filed: Jun. 29, 1992

[51] Int. Cl.$^5$ .................. A61K 31/44; C07D 495/08
[52] U.S. Cl. ..................... 514/338; 546/270
[58] Field of Search .................. 546/270; 514/338

[56] References Cited

FOREIGN PATENT DOCUMENTS 63-216890  9/1988  Japan .
63-277683 11/1988  Japan .

OTHER PUBLICATIONS

Wade Jr. Organic Chemistry 1987 Prentice-Hall, Inc. p. 349.
Zeffren et al. The Study of Enzyme Mechanism p. 87, 1974.
Su et al., C.A. 101(g): 72492p 1984.
Kozikowski et al., Amer. Chem. Soc., 104, 7622–7626, 1982.

Primary Examiner—Jane T. Fan
Attorney, Agent, or Firm—Mollie M. Yang; David L. Rose

[57] ABSTRACT

Compounds having the formula I:

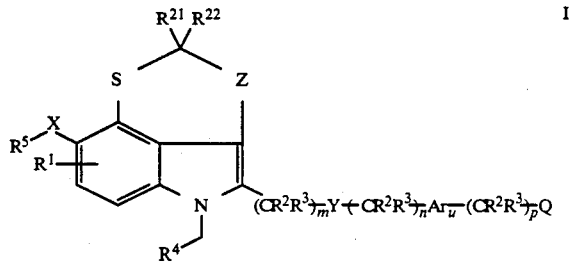

are inhibitors of the 5-lipoxygenase enzyme and inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, psoriasis, uveitis, and allograft rejection and in preventing the formation of atherosclerotic plaques.

3 Claims, No Drawings

ARYL THIOPYRANO[4,3,2-CD]INDOLES AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated as $LTB_4$), $LTC_4$, $LTD_4$, and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

A few derivatives of the natural product chuangxinmycin, which contains the thiopyrano [4,3,2-c,d]indole ring system, have been described as showing antibiotic and anticancer utilities. However, the substitution pattern is very different from the present compounds. The compounds of the present invention have complex substituents at positions 2 and 6, whereas such substitution is for the most part absent or very simple in the thiopyrano[4,3,2-c,d]indoles described in the literature. The following structures and references are illustrative of the compounds in the prior art.

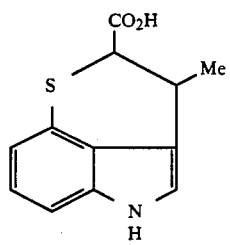

Chuangxinmycin

Kozikowski et al., J. Am. Chem. Soc., 104, 7622-26, 1982.
Matsumoto et al. Japan Kokai Tokkyo Koho 63-216890

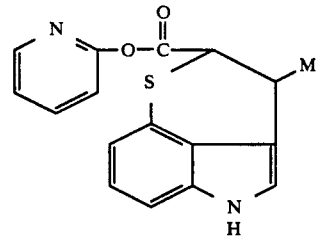

Chuangxinmycin 2-pyridinyl ester

Su et al., Yiyao Gougye, pp. 17-21, 1984 [Chem. Abst., 101, no. 72492]

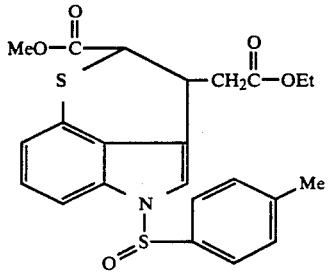

Matsumoto et al., Japan Kokai Tokkyo Koho, 63-277683

SUMMARY OF THE INVENTION

The present invention relates to certain aryl thiopyrano[4,3,2-cd]indoles having activity as 5-lipoxygenase (5-LO) inhibitors and leukotriene biosynthesis inhibitors, to methods for their preparation, and to methods and pharmaceutical formulations for using these compounds in mammals (especially humans).

Because of their activity as 5-LO inhibitors and as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection, and in preventing the formation of atherosclerotic plaques.

DETAILED DESCRIPTION OF THE INVENTION

The present invention provides novel compounds of the Formula I:

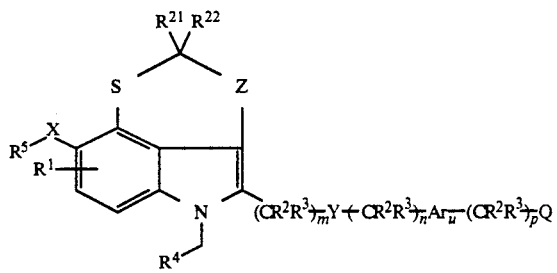

wherein:

$R^1$ is H, lower alkyl, cycloalkyl, lower alkoxy, perhalo lower alkenyl, CN, $NO_2$, $CF_3$, $N_3$, $N(R^6)_2$, $NR^6COR^7$, $NR^6CON(R^6)_2$, $OR^6$, $SR^8$, $S(O)R^8$, $S(O)_2R^8$, $S(O)_2N(R^6)_2$, $COR^7$, $CON(R^6)_2$, $CO_2R^9$, or halogen;

$R^2$ is H, lower alkyl, hydroxy, or lower alkoxy, or two $R^2$ groups on adjacent carbon atoms may be a bond;

$R^3$ is H or lower alkyl;

$R^4$ is H, $[aryl(R^{10})_2]_t$, alkyl, cycloalkyl, lower alkenyl, phenyl lower alkenyl, perhalophenyl, or substituted lower alkyl wherein the substituent is $[aryl(R^{10})_2]_t$, phenoxy, or N-morpholino;

$R^5$ is $[aryl(R^{10})_2]_t$ or substituted lower alkyl wherein the substituent is $[aryl(R^{10})_2]_t$;

$R^6$ is H or lower alkyl, or two $R^6$ groups attached to the same nitrogen may form a saturated ring of 5 or 6 members, optionally containing a second heteroatom chosen from O, S, and $NR^2$;

$R^7$ is H, lower alkyl, phenyl, p-tolyl, or $CF_3$;

$R^8$ is lower alkyl, phenyl, p-tolyl, or $CF_3$;

$R^9$ is H, lower alkyl, or benzyl;

$R^{10}$ is H, lower alkyl, cycloalkyl, lower alkoxy, benzyl, benzyloxy, perhalo lower alkenyl, CN, $NO_2$, $CF_3$, $N_3$, $N(R^6)_2$, $NR^6COR^7$, $NR^6CON(R^6)_2$, $OR^6$, $SR^8$, $S(O)R^8$, $S(O)_2R^8$, $S(O)_2N(R^6)_2$, $COR^7$, $CON(R^6)_2$, $CO_2R^9$, halogen, hydroxy- or lower alkoxy-tetrahydropyranyl, or 1-hydroxy- or 1-lower alkoxy-1-thiazol-2,4, or 5-yl lower alkyl;

$R^{11}$ is H, lower alkyl, lower alkoxy, lower alkylthio, halogen, CN, or $CF_3$;

$R^{12}$ is lower alkyl, $R^{10}$-phenyl, $CF_3$, or $N(R^6)_2$;

$R^{13}$ is $CO_2H$, $N(R^6)_2$, or $NHCOR^7$;

$R^{14}$ is —(CH$_2$)$_s$—C(R$^{15}$)$_2$—(CH$_2$)$_s$—R$^{16}$ or —CH$_2$CON(R$^{18}$)$_2$;

$R^{15}$ is H or lower alkyl;

$R^{16}$ is a) a monocyclic or bicyclic heterocyclic radical containing from 3 to 12 nuclear carbon atoms and 1 or 2 nuclear heteroatoms selected from N, S, and O and with each ring in the heterocyclic radical being formed of 5 or 6 atoms, or b) the radical V—R$^{17}$;

$R^{17}$ contains up to 20 carbon atoms and is (1) an alkyl group or (2) an alkyl carbonyl group of an organic acyclic or monocyclic carboxylic acid containing not more than 1 heteroatom in the ring;

$R^{18}$ is H or lower alkyl or two R$^{18}$ groups attached to the same nitrogen may form a saturated ring of 5 or 6 members, optionally containing a second heteroatom chosen from O, S, and NR$^2$;

$R^{19}$ is H, lower alkyl, lower alkylcarbonyl, or lower alkylsulfonyl;

$R^{20}$, $R^{21}$, and $R^{22}$ is each independently H or lower alkyl;

$R^{23}$ is lower alkyl or benzyl;

$R^{24}$ is H or lower alkyl or two R$^{24}$ groups attached to the same carbon may form a ring of 3 to 8 members;

Q is CO$_2$R$^9$, CO$_2$R$^{14}$, CN$_4$H, —OH, —CH$_2$OH, —CHO, —CON(R$^6$)$_2$, —CON(OH)R$^6$, —CONHS(O)$_2$R$^{12}$, —COCN$_4$H, —CONR$^6$(CH$_2$)$_r$R$^{13}$, —N(R$^6$)$_2$, —NHCOR$^7$, S(O)$_2$NHCOR$^{12}$, —NHS(O)$_2$R$^{12}$, —NHCOCO$_2$R$^9$, —CONHCN, or —CONHCN$_4$H;

U is CHR$^{20}$, O, or S;

V is O, S, or NR$^9$;

W is O, S, or NR$^6$;

X is —(C(R$^{24}$)$_2$)$_q$U—, —CR$^{20}$=CR$^{20}$—, or —C(R$^{24}$)$_2$OC(R$^{24}$)$_2$—;

Y is a bond, O, S, NR$^{19}$, or CONR$^9$;

Z is CHR$^{20}$, CHWR$^6$, or CO;

m is 0 to 3;

n is 0 to 3;

p is 0 to 3;

q is 0 to 3;

r is 1 to 3;

s is 0 or 1;

t is 1 or 2;

u is 0 or 1;

Ar is arylene (R$^{11}$)$_2$, wherein arylene is phenylene, furandiyl, thiendiyl, or naphthalenediyl;

aryl is phenyl, pyridinyl, quinolinyl, or benzothiazolyl or the N-oxides thereof;

or a pharmaceutically acceptable salt thereof.

A preferred embodiment of the present invention is represented by Formula Ia:

$R^{10}$ is H, lower alkyl, or halogen;

Q is —CO$_2$H, CN$_4$H, or —CONHS(O)$_2$R$^{12}$;

Y is a bond, O, or S;

the remaining substituents are as defined for Formula I;

or a pharmaceutically acceptable salt thereof.

DEFINITIONS

The following abbreviations have the indicated meanings:

Ac=acetyl
Bt=benzothiazolyl
Bz=benzyl
DEAD=diethyl azidodicarboxylate
DMAP=4-(dimethylamino)pyridine
DMF=dimethylformamide
DMPU=1,3-dimethyl-3,4,5,6-tetrahydro-2(1H)-pyrimidinone
Et=ethyl
Fur=furandiyl
HMPA=hexamethylphosphoric triamide
Me=methyl
Ph=phenyl
Phe=benzenediyl
Py=pyridyl
Pye=pyridinediyl
Qu=quinolinyl
r.t.=room temperature
t-Bu, t-butyl=tertiary butyl
Th=2- or 3-thienyl
TFA=trifluoroacetic acid
THF=tetrahydrofuran
Thi=thienediyl
TLC=thin layer chromatography
CN$_4$H=1H (or 2H)-tetrazol-5-yl
C$_3$H$_5$=allyl.

The term "alkyl" includes "lower alkyl" and extends to cover carbon fragments having up to 20 carbon atoms, and includes linear and branched structures and combinations thereof. Examples of alkyl groups include octyl, nonyl, undecyl, dodecyl, tridecyl, tetradecyl, pentadecyl, eicosyl, 3,7-diethyl-2,2-dimethyl-4-propylnonyl, and the like.

The term "lower alkyl" means alkyl groups of from 1 to 7 carbon atoms. Examples of lower alkyl groups include methyl, ethyl, propyl, isopropyl, butyl, sec- and tert-butyl, pentyl, hexyl, heptyl, and the like.

The term "cycloalkyl" means a hydrocarbon containing one or more rings having from 3 to 12 carbon atoms, with the hydrocarbon having up to a total of 20 carbon atoms. Examples of cycloalkyl groups are cyclopropyl, cyclopentyl, cycloheptyl, adamantyl, cyclododecylmethyl, 2-ethyl-1-bicyclo[4.4.0]decyl, and the like.

The term "perhalo" means one or more hydrogen

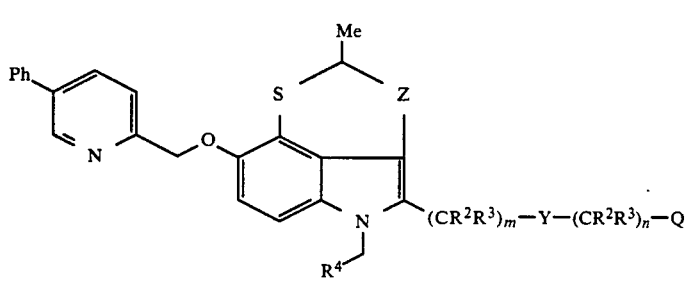

Ia wherein:
$R^4$ is [aryl(R$^{10}$)$_2$]$_t$;

atoms are replaced by halogen atoms.

"Lower alkenyl" groups mean alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, and the like.

The term "lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Alkylcarbonyl" means alkylcarbonyl groups of 1 to 20 carbon atoms of a straight, branched or cyclic configuration. Examples of alkylcarbonyl groups are 2-methylbutanoyl, octadecanoyl, 11-cyclohexylundecanoyl, and the like. Thus, the 11-cyclohexylundecanoyl group is c—Hex—$(CH_2)_{10}$—C(O)—.

Halogen includes F, Cl, Br, and I.

It is intended that the definitions of any substituent (e.g., $R^1$, $R^2$, $R^6$, etc.) in a particular molecule be independent of its definitions elsewhere in the molecule. Thus, $(R^6)_2$ represents —NHH, —NHMe, —N(Me)(Et), etc.

The heterocycles formed when two $R^6$ (or $R^{18}$) groups join through N include pyrrolidine, piperidine, morpholine, thiamorpholine, piperazine, and N-methylpiperazine.

The prodrug esters of Q (i.e., when $Q=CO_2R^{14}$) are intended to include the esters such as are described by Saari et al., J. Med. Chem., 21, No. 8, 746-753 (1978), Sakamoto et al., Chem, Pharm. Bull., 32, No. 6, 2241-2248 (1984) and Bundgaard et al., J. Med. Chem., 30, No. 3, 451-454 (1987). Within the definition of $R^{16}$, some representative monocyclic or bicyclic heterocyclic radicals are:

2,5-dioxo-1-pyrrolidinyl,
(3-Pyridinylcarbonyl)amino,
1,3-dihydro-1,3-dioxo-2H-isoindol-2-yl,
1,3-dihydro-2H-isoindol-2-yl,
2,4-imidazolinedion-1-yl,
2,6-piperidinedion-1-yl,
2-imidazolyl,
2-oxo-1,3-dioxolen-4-yl,
piperidin-1-yl,
morpholin-1-yl, and
piperazin-1-yl.

OPTICAL ISOMERS-DIASTEREOMERS-GEOMETRIC ISOMERS

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

SALTS

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Mixed salts may at times be advantageous. For example the sodium salt of certain examples of compound I when mixed with an equivalent amount of tromethamine yields a more soluble salt form of I.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

UTILITIES

The ability of the compounds of Formula I to inhibit the 5-lipoxygenase enzyme and to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, and 16) metastasis of tumors.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol- induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

DOSE RANGES

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

PHARMACEUTICAL COMPOSITIONS

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200; and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |
| Tablet | mg/tablet |
| Compound of Formula I | 25 |
| Microcrystalline Cellulose | 415 |
| *-continued* | |
| Povidone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

COMBINATIONS WITH OTHER DRUGS

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives;
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

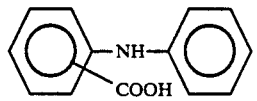

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

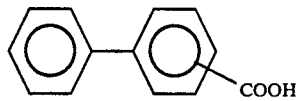

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

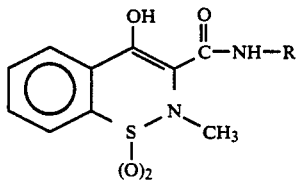

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an H$_1$ or H$_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a K+/H+ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, Vol. 316, pages 126-131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

METHODS OF SYNTHESIS

Compounds of the formula I of the present invention may be prepared according to the synthetic routes outlined in the Schemes I to III and by following the methods described herein.

SCHEME 1

Scheme 1 describes the synthesis of compounds of formula IA. The indole intermediate IV may be prepared by a Fisher-Indole condensation between hydrazine II and ketone III in an organic solvent such as toluene in the presence of an organic acid such as acetic acid. Transformation of IV into its acid chloride may be effected by treatment of a solution of IV in a solvent such as methylene chloride with oxalyl chloride and a catalytic quantity of N,N-dimethyl formamide. Cyclization of this acid chloride may be accomplished by a Friedel-Crafts process using a Lewis acid such as aluminum chloride as catalyst. This cyclization is accompanied by a structural rearrangement which leads to the ketone V.

Reduction of this ketone may be effected via a reducing agent such as sodium cyanoborohydride in the presence of a Lewis acid such as zinc iodide in an organic solvent such as 1,2-dichloroethane to afford VI. Reduction of the ester function of VI to the corresponding alcohol VII results from reaction with an appropriate reducing agent such as lithium aluminum hydride in an ether solvent such as tetrahydrofuran. Demethylation of VII using, for example, sodium t-butyl thiolate in hot DMF affords the phenol VIII, which may be alkylated with an aryl methyl halide, $R^5CH_2X^1$, in the presence of an inorganic base such as cesium carbonate in acetonitrile or a similar polar solvent, to afford the ether alcohol IX. Treatment of this compound with a haloalkanoic acid, $X^1(CR^2R^3)_nCO_2H$, in the presence of a strong base such as sodium hydride, in a solvent such as THF, leads to final compound IA.

Compound IA can also be prepared by treatment of a solution of the alcohol IX in DMSO (or another appropriate organic solvent) with an inorganic base (e.g. sodium hydride and haloalkanoic acid ester, $X^1(CR^2R^3)_nCO_2R^{23}$, to provide the ester X which upon hydrolysis under standard conditions affords compound IA.

SCHEME II

Scheme II outlines the synthesis of compounds of formula IB. In a fashion similar to Scheme I, hydrazine II is condensed with ketone XI to afford indole XII. Desulfenylation can be achieved in a strong proton acid such as trifluroacetic acid in the presence of a thiol such as thiosalicylic acid to afford intermediate XIII, which may be resulfenylated with an appropriate sulfenyl chloride to afford sulfide XIV. Mild basic hydrolysis, via a dilute aqueous base such as LiOH, selectively affords the mono acid XV which can be cyclized as described in Scheme I, with a similar structural rearrangement, to the ketone XVI. Demethylation, using for example sodium t-butyl thiolate in hot DMF, followed by esterification with diazomethane, affords the phenol ester XVII. Coupling of XVII with $R^5CH_2X^1$, as described in Scheme I, leads to ether derivative XVIII which may be conveniently saponified using an aqueous solution of an inorganic base such as NaOH to obtain the final acid IB.

SCHEME III

Scheme III describes the synthesis of compounds of formula I starting with the thiopyranoindole IX (from Scheme I). In the case where m>1 the alcohol of compound IX may be transformed to the bromo derivative XIX by reaction with triphenylphosphine and carbon tetrabromide in an organic solvent such as chloroform. Displacement of the bromine of compound XIX with an appropriate nucleophile, $NaSAr(CR^2R^3)_pCO_2R^{23}$ (generated using sodium hydride in DMF), followed by hydrolysis, provides compounds of formula IC. For the alcohol IX where m=1, brief treatment of this alcohol in an organic solvent (e.g., 1,2-dichloroethane) with boron trifluoride etherate and the thiol acid $HSAr(CR^2R^3)_pCO_2H$ leads to compounds of formula ID.

Treatment of the alcohol of compound IX with a phosphine such as triphenylphosphine, a coupling reagent (e.g., DEAD) and a phenolic ester, $HOAr(CR^2R^3)_pCO_2R^{23}$, in an organic solvent like THF gives rise to the ester XX. Saponification of ester XX using an inorganic base (e.g., lithium hydroxide) in aqueous methanol/THF yields IE. The alcohol IX may be converted to the nitrile derivative XXI by sequential treatment with an inorganic base (e.g., sodium hydride) and an alkylating agent $(Br(CR^2R^3)_nArCN)$ in an organic solvent such as DMF. The nitrile XXI may then be hydrolysed using an inorganic base such as potassium hydroxide in a high boiling organic solvent (e.g., ethylene glycol and 2-(ethoxyethoxy) ethanol) to provide the acid of formula IF. Alternatively, the nitrile XXI on heating in a high boiling organic solvent (for example, 1,2-dichlorobenzene) with tri-n-butyltin azide affords the tetrazole derivative IG, a representative of compound I.

SCHEME I
PREPARATION OF FORMULA I COMPOUNDS
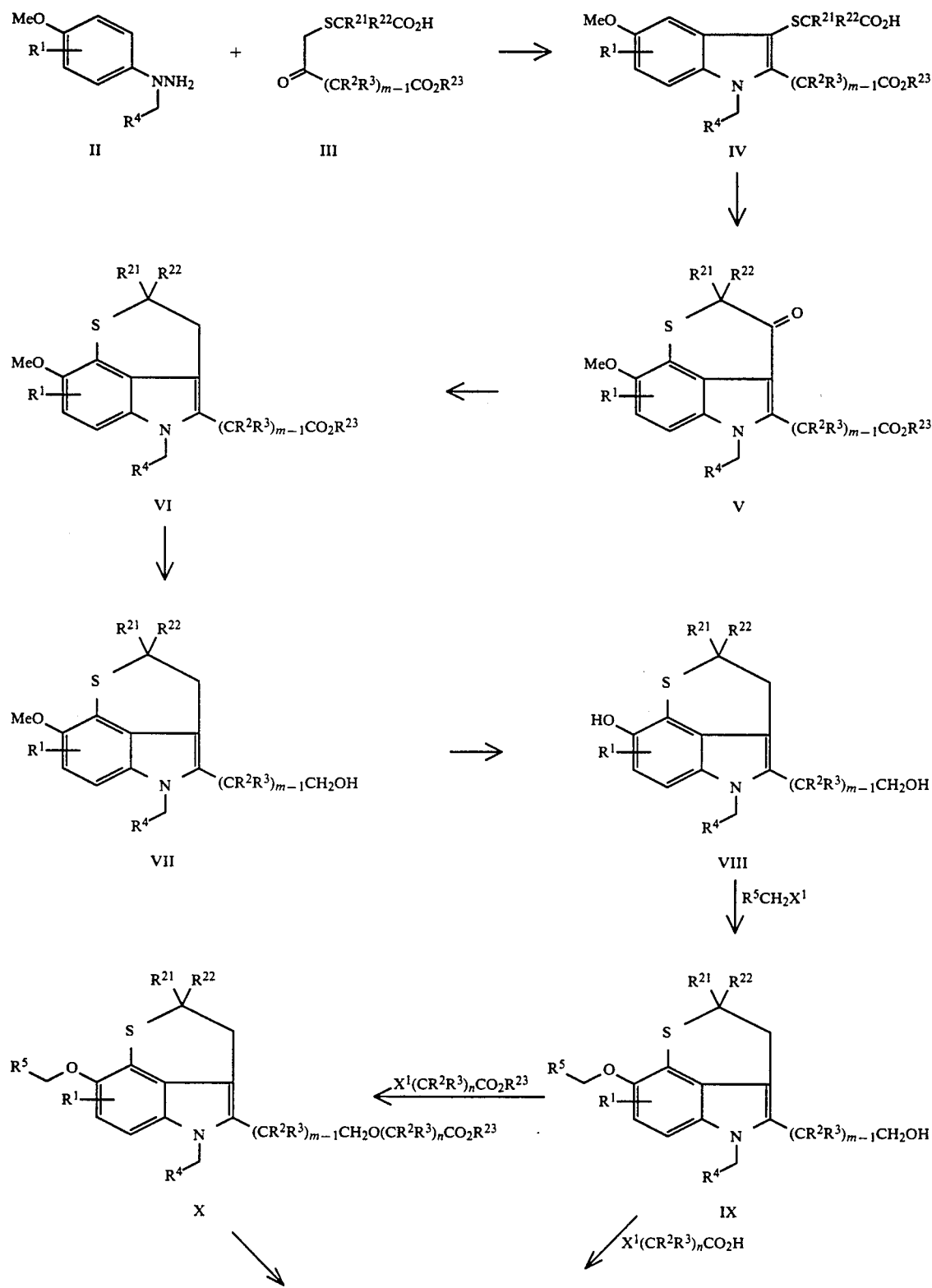

-continued
SCHEME I
PREPARATION OF FORMULA I COMPOUNDS
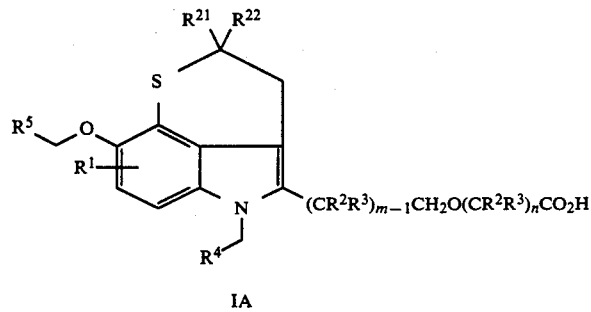
IA
SCHEME II
PREPARATION OF FORMULA I COMPOUNDS
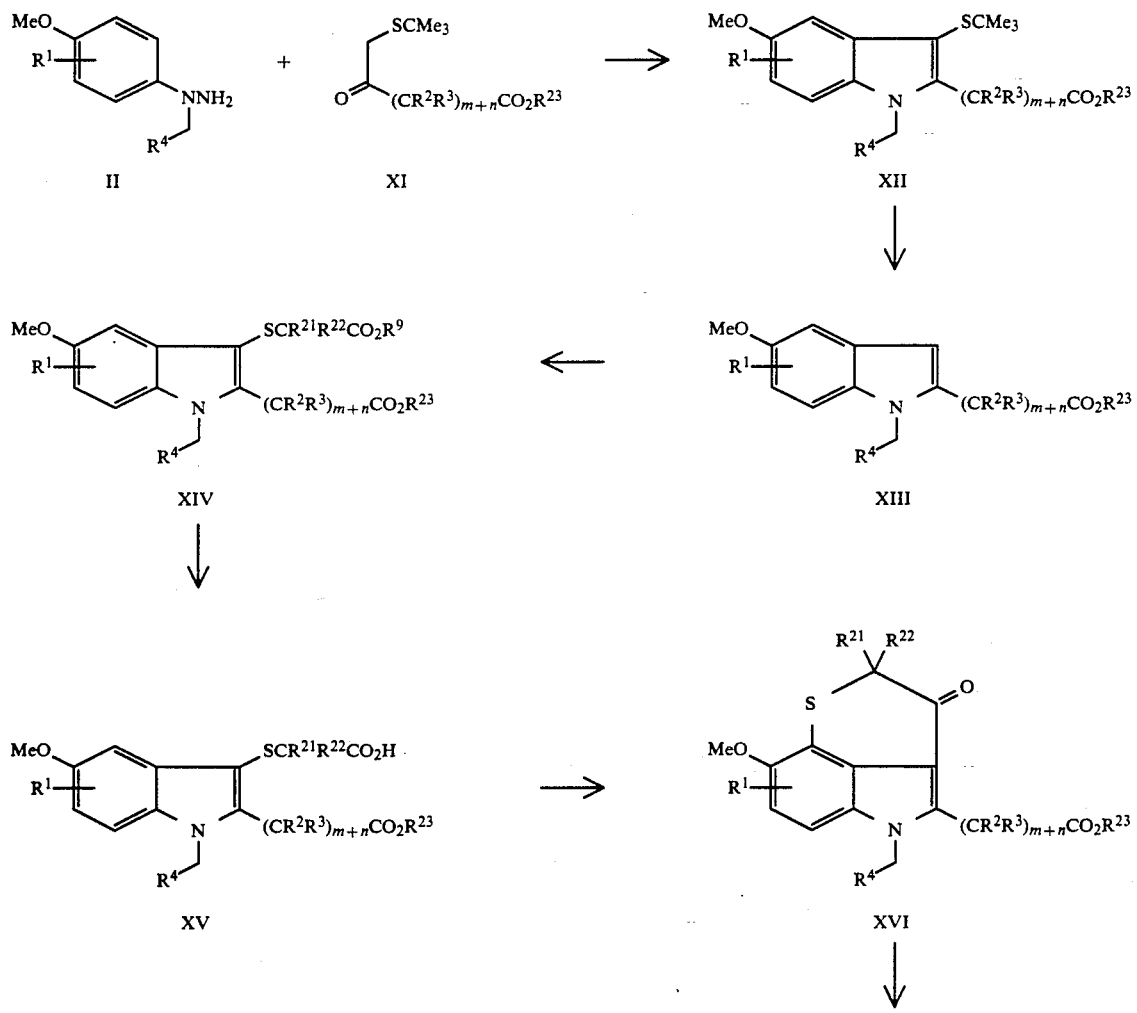

-continued
SCHEME II
PREPARATION OF FORMULA I COMPOUNDS
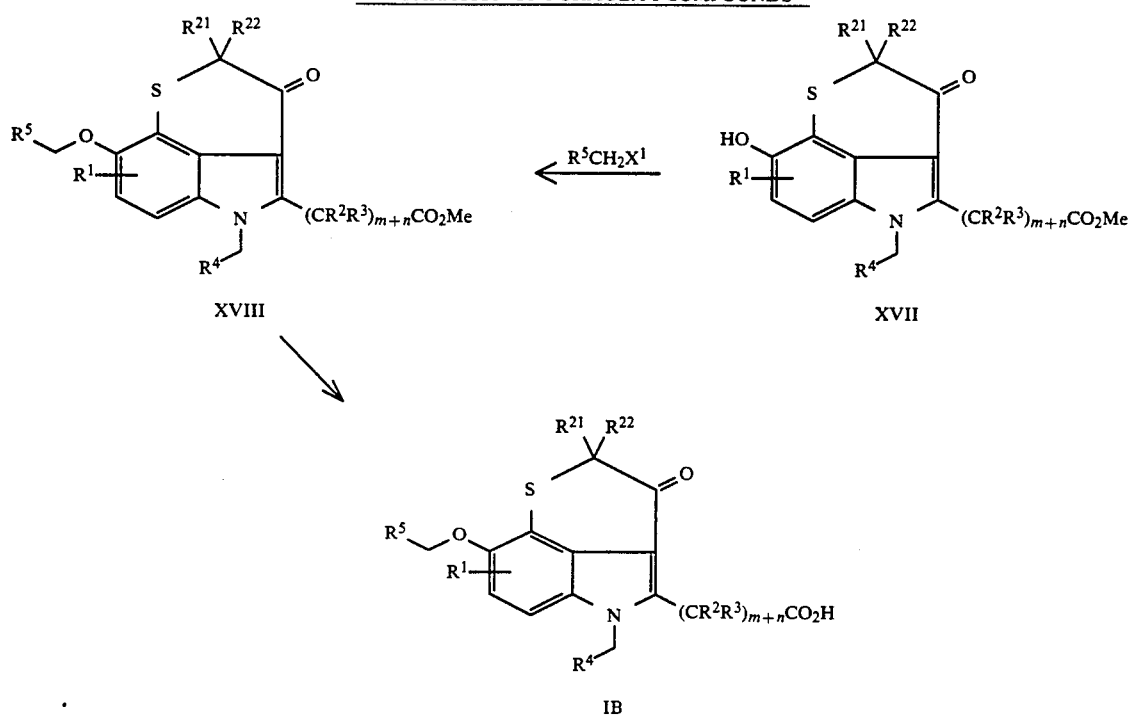
SCHEME III
PREPARATION OF FORMULA I COMPOUNDS
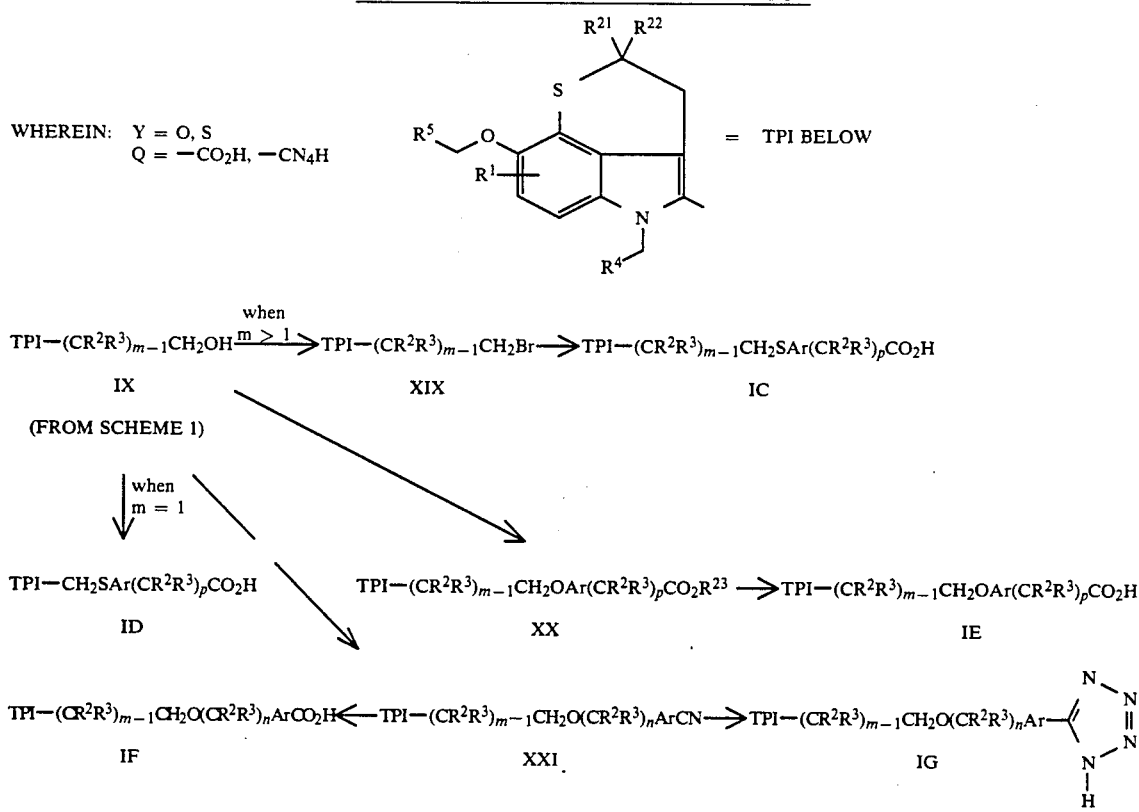
Table I illustrates compounds of the present invention:

TABLE I

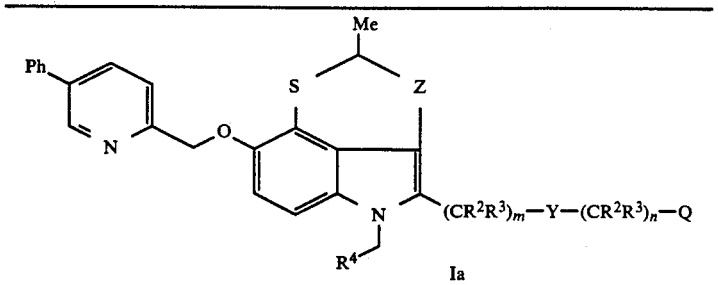

| Ex | R⁴ | Z | $(CR^2R^3)_m$ | Y | $(CR^2R^3)_n$ | Q |
|----|------|-----|---------|---|---------|-----|
| 1. | 4-Cl—Ph | $CH_2$ | $CH_2CH_2$ | O | CH(Et) | $CO_2H$ |
| 2. | 4-Cl—Ph | CO | — | — | $CH_2C(Me)_2$ | $CO_2H$ |
| 3. | 3-Py | $CH_2$ | $CH_2$ | S | $(CH_2)_3$ | $CO_2H$ |
| 4. | 2-Qu | $CH_2$ | — | — | $CH_2C(Me)_2$ | $CN_4H$ |
| 5. | 5-Bt | $CH_2$ | CH(Me) | O | $C(Me)_2CH_2$ | $CONHS(O)_2Ph$ |
| 6. | 3-F—Ph | $CH_2$ | — | — | $CH_2C(Me)_2$ | $CO_2H$ |

ASSAYS FOR DETERMINING BIOLOGICAL ACTIVITY

Compounds of Formula I can be tested using the following assays to determine their mammalian leukotriene biosynthesis inhibiting activity.

DETERMINATION OF INHIBITION OF RAT 5-LIPOXYGENASE

The activity of 5-lipoxygenase is measured from the conversion of [$^{14}$C]-arachidonic acid to 5-HETE and 5,12-diHETEs catalyzed by the 10,000x g supernatant fraction from rat PMN leukocytes, using the procedure of Riendeau and Leblanc (*Biochem. Biophys. Res. Commun.*, 141, 534–540, 1986) with minor modifications. The incubation mixture contains 25 mM Na$^+$/K$^+$ phosphate buffer, pH 7.3, 1 mM ATP, 0.5 mM CaCl$_2$, 0.5 mM mercaptoethanol and an aliquot of the enzyme preparation in a final volume of 0.2 mL. The enzyme is pre-incubated with the inhibitor for 2 min at 37° C. before initiation of the reaction with the addition of 2 mL of [$^{14}$C]-arachidonic acid (25,000 DPM) in ethanol to obtain a final concentration of 10 mM. Inhibitors are added as 500-fold concentrated solutions in DMSO. After incubation for 10 min at 37° C., the reaction is stopped by adding 0.8 mL of diethyl ether/methanol/1M citric acid (30:4:1). The samples are centrifuged at 1,000x g for 5 min and the organic phases analyzed by TLC on Baker Si250F-PA or Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs is determined using a Berthold TLC analyzer LB 2842. The activity of 5-lipoxygenase is calculated from the percentage of conversion of arachidonic acid to 5-HETE and 5,12-diHETEs after the 10 min incubation.

HUMAN POLYMORPHONUCLEAR (PMN) LEUKOCYTE LTB$_4$ ASSAY

A. Preparation of Human PMN.

Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum, A. *Scand. J. Clin. Lab. Invest*, 21 (Supp 97), 77 (1968). Contaminating erythrocytes are removed by lysis following exposure to ammonium chloride (0.16M) in Tris buffer (pH 7.65), and the PMNs resuspended at 5×10$^5$ cells/mL in HEPES (15 mM)-buffered Hanks balanced salt solution containing Ca$^{2+}$ (1.4 mM) and Mg$^{2+}$ (0.7 mM), pH 7.4. Viability is assessed by Trypan blue exclusion.

B. Generation and Radioimmunoassay of LTB$_4$.

PMNs (0.5 mL; 2.5×10$^5$ cells) are placed in plastic tubes and incubated (37° C., 2 min) with test compounds at the desired concentration or vehicle (DMSO, final concentration 0.2%) as control. The synthesis of LTB$_4$ is initiated by the addition of calcium ionophore A23187 (final concentration 10 mM) or vehicle in control samples and allowed to proceed for 5 minutes at 37° C. The reactions are then terminated by the addition of cold methanol (0.25 mL) and samples of the entire PMN reaction mixture removed for radioimmunoassay of LTB$_4$.

Samples (50 mL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer are added to reaction tubes. Thereafter [$^3$H]-LTB$_4$ (10 nCi in 100 mL RIA buffer) and LTB$_4$-antiserum (100 mL of a 1:3000 dilution in RIA buffer) are added and the tubes vortexed. Reactants are allowed to equilibrate by incubation overnight at 4° C. To separate antibody-bound from free LTB$_4$, aliquots (50 mL) of activated charcoal (3% activated charcoal in RIA buffer containing 0.25% Dextran T-70) are added, the tubes vortexed, and allowed to stand at room temperature for 10 minutes prior to centrifugation (1500x g; 10 min; 4° C.). The supernatants containing antibody-bound LTB$_4$ are decanted into vials and Aquasol 2 (4 mL) added. Radioactivity is quantified by liquid scintillation spectrometry. The specificity of the antiserum and the sensitivity of the procedure have been described by Rokach et al. *Prostaglandins Leukotrienes and Medicine* 13, 21 (1984). The amount of LTB$_4$ produced in test and control (approx. 20 ng/10$^6$ cells) samples is calculated. Inhibitory dose-response curves are constructed using a four-parameter algorithm and from these the IC$_{50}$ values are determined.

PREPARATION OF KETONES

Ketone 1

Ethyl 4-(α-carboxyethylthio)acetoacetate

To a solution of thiolactic acid (117 g, 1.10 mol) in THF (1800 mL) there was added diisopropylethyl amine (284 g, 2.2 mol) and then, dropwise, ethyl 4-chloroacetoacetate (165 g, 1.0 mol). The resulting mixture was stirred at r.t. overnight. After filtration, the filtrate was evaporated, the residue was diluted with water (1 L) and conc'd HCl was added until no more cloudiness resulted on further addition. The mixture was extracted 3× with Et$_2$O, the combined extracts were washed 4× with brine, dried over Na$_2$SO$_4$, and evaporated. The residual yellow oil was used as such without further purification.

Ketone 2

Methyl 5-t-butylthio-2,2-dimethyl-4-oxopentanoate

This compound was prepared as described in U.S. Pat. No. 5,081,138, preparation 4.D (Jan. 14, 1992).

PREPARATION OF 5-PHENYL-2-PICOLYL CHLORIDE

Step 1

5-Phenyl-2-picoline

A suspension of 100 g of wet Raney Nickel in 1.5 L of dodecanol in a three-neck round bottom flask equipped with a Dean Stark apparatus was heated until the temperature reached 130° C., then 3-phenylpyridine (Aldrich) was added and the reaction was heated at 190°–200° C., for 6 hours. During the reaction, water was constantly eliminated. When the reaction was over, half of the dodecanol was removed by distillation. After cooling the reaction mixture to r.t., 200 mL of H$_2$O and 400 mL of hexane were added, the mixture was shaken and the hexane layer decanted. This process was repeated several times. The combined hexane fractions were washed with 10N HCl until the disappearance of 5-phenyl-2-picoline from the organic phase. The combined aqueous layers were filtered, washed with hexane, basified with 10N NaOH, and extracted with CH$_2$Cl$_2$. The organic layer was washed with NH$_4$OAc (25%), dried over MgSO$_4$ and evaporated to dryness. The crude residue was then distilled under vacuum (100° C. at 0.1 mm of Hg) to afford the pure title product.

Step 2

5-Phenyl-2-picolyl chloride

To a solution of 5-phenyl-2-picoline (6.2 g) in CCl$_4$ (250 mL) were added N-chlorosuccinimide (5.85 g) and benzoylperoxide (100 mg). The reaction was then heated to reflux and irradiated with a 225 watt lamp for 5 hours. After cooling, Et$_2$O was added, the solid filtered and the filtrate was evaporated to dryness. The crude residue was chromatographed on silica gel (hexane/EtOAc 9:1) to give the pure title product.

PREPARATION OF BIS(α-CARBOMETHOXYETHYL)DISULFIDE

To a solution of thiolactic acid (26.5 g) in 1N aq NaOH (700 mL) and EtOH (50 mL) there was added a solution of 0.3M I$_2$ in EtOH until the color of I$_2$ remained. The mixture was filtered, the filtrate was acidified with 6N HCl and extracted 4× with EtOAc. These extracts were washed 4× with brine, dried over Na$_2$SO$_4$ and evaporated down to a yellow oil which solidified. This product was dissolved in MeOH (900 mL) and, at 0° C. there was slowly added SOCl$_2$ (44.6 g). The mixture was stirred overnight at r.t., then evaporated. The residue was dissolved in EtOAc, the solution washed 5× with brine, dried and evaporated to afford the title compound as a yellow oil.

EXAMPLE 1

2-{2-[5-(4-Chlorobenzyl)-2-methyl-8-(5-phenylpyridin-2-ylmethoxy)-3,5-dihydro-2H-thiopyrano[4,3,2-cd]indol-4-yl]ethoxy}-butanoic acid Step 1: Ethyl 3-(α-carboxyethyl)-1-(4-chlorobenzyl)-5-methoxyindole-2-acetate A mixture of Ketone 1 (47 g, 0.20 mol), 1-(4-chlorobenzyl)-1-(4-methoxyphenyl)hydrazine hydrochloride [U.S. Pat. No. 5,081,145, Table 3, cmpd. 10 (Jan. 14, 1992)] (67 g, 0.22 mol), HOAc (60 mL), and toluene (1.1 L) was mechanically stirred for 5 days at r.t.

Water (500 mL) was added to the mixture and after 15 min., the solid was filtered, washed with toluene and H$_2$O, and dried to afford the title product; m.p. 163°–165° C.

Step 2: Ethyl 5-(4-chlorobenzyl)-8-methoxy-2-methyl-3,5-dihydro-3-oxo-2H-thiopyrano[4,3,2-cd]indole-4-acetate To a suspension of product from Step 1 (25 g, 54 mmol) in CH$_2$Cl$_2$ (300 mL) there was added oxalyl chloride (9.6 g, 75.6 mmol) and then DMF (3 drops). The mixture was stirred at r.t. for one hour. To this red solution, cooled to 0° C., there was slowly added AlCl$_3$ 1.9M in nitrobenzene (72 mL, 136.8 mmol) and the resulting dark mixture was stirred at 0° for 4 hours. Iced H$_2$O was added and the mixture was extracted 4× with CH$_2$Cl$_2$. The combined extracts were washed 4× with H$_2$O, dried and evaporated. The residue was chromatographed over silica, eluting first with a 1:9 mixture of EtOAc and hexane to remove the nitrobenzene, then with a 1:2 mixture of the same solvents to collect the desired cyclized product as a cream-colored solid after trituration with hexane and filtration.

Step 3: Ethyl 5-(4-chlorobenzyl)-8-methoxy-2-methyl-3,5-dihydro-2H-thiopyrano[4,3,2-cd]indole-4-acetate To a suspension of product from Step 2 (886 mg) in 1,2-dichloroethane (16 mL) there was added ZnI$_2$ (960 mg) and NaCNBH$_3$ (440 mg). The mixture was heated to 60° for 1 hour, cooled, diluted with CH$_2$Cl$_2$, washed 3× with H$_2$O, dried over Na$_2$SO$_4$, filtered and evaporated to afford the title product as an oil which slowly solidified. It was used as such in the next step.

Step 4: 5-(4-Chlorobenzyl)-4-(2-hydroxyethyl)-8-methoxy-2-methyl-3,5-dihydro-2H-thiopyrano[4,3,2-cd]indole To a solution of product from Step 3 (785 mg, 1.83 mmol) in THF (30 mL), cooled to 0° C. and under N$_2$ atmosphere, there was added LiAlH$_4$ (152 mg, 4 mmol). The resulting mixture was stirred at 0° C. for 30 minutes, then quenched carefully with ice-cold H$_2$O, and acidified with 1N aq HCl (10 mL). The mixture was extracted twice with Et$_2$O, and these extracts were washed 3× with brine, dried over Na$_2$SO$_4$, and evaporated. The residue was chromatographed, eluting with a 1:1 mixture of EtOAc and hexane, to afford the title product as a thick oil.

Step 5: 5-(4-Chlorobenzyl)-8-hydroxy-4-(2-hydroxyethyl)-2-methyl-3,5-dihydro-2H-thiopyrano[4,3,2-cd]indole To a suspension of 97% NaH (120 mg, 4.88 mmol) in DMF (10 mL) and DMPU (1 mL) cooled to 0° C., there was added 2-methyl-2-propanethiol (550 mg, 6.10 mmol) and the resulting mixture was stirred at 0° C. for one hour. To this clear solution there was added a solution of product from Step 4 (490 mg, 1.22 mmol) in DMF (4 mL). The mixture was heated at 140° C. for 19 hours, cooled, diluted with $H_2O$, acidified with 1N HCl and extracted 3× with $Et_2O$. These extracts were washed 2× with brine, dried, and evaporated. The residue was chromatographed on silica gel, eluting with a 1:1 mixture of EtOAc and hexane, to afford the title product as a thick oil.

Step 6: 5-(4-Chlorobenzyl)-4-(2-hydroxyethyl)-2-methyl-8-(5-phenylpyridin-2-ylmethoxy)-3,5-dihydro-2H-thiopyrano[4,3,2-cd]indole A mixture of product from Step 5 (150 mg, 0.39 mmol), 5-phenyl-2-picolyl chloride (95 mg, 0.47 mmol) and $Cs_2CO_3$ (152 mg, 0.47 mmol) in $CH_3CN$ (5 mL) was stirred at r.t. for 20 hours, then at 60° C. for 1.5 hours. The mixture was diluted with EtOAc (25 mL), washed 3× with $H_2O$, dried over $Na_2SO_4$, and evaporated. The residue was chromatographed on silica gel, eluting with a 1:1 mixture of EtOAc and hexane, to afford the title product as an oil which solidified.

Step 7: 2-[2-[5-(4-Chlorobenzyl)-2-methyl-8-(5-phenylpyridin-2-ylmethoxy)-3,5-dihydro-2H-thiopyrano[4,3,2-cd]indol-4-yl]ethoxy]butyric acid To a solution of product from Step 6 (130 mg, 0.23 mmol) in THF (2 mL) there was added 97% NaH (23 mg, 1 mmol) and the mixture was stirred at r.t. for 15 min. There was added a solution of 2-bromobutyric acid (84 mg, 0.5 mmol) in THF (1.5 mL) and the mixture was refluxed for 20 hours. After cooling, there was added more NaH (46 mg) and 2-bromobutyric acid (170 mg) and the mixture was refluxed for a further 24 hours. The cooled mixture was diluted with $H_2O$, made strongly basic with 1N aq NaOH, and extracted twice with $Et_2O$. The aqueous fraction was then acidified with 1N HCl and extracted 3× with EtOAc. The crude product thus obtained was purified by esterification with ethereal diazomethane and the resulting ester chromatographed on preparative TLC silica gel plates, eluting with a 1:4 mixture of EtOAc and toluene. After extraction of the silica with EtOAc, the purified ester (54 mg) was hydrolyzed. It was dissolved in THF (1.5 mL) and MeOH (1.5 mL) and there was added 1M aq LiOH (0.8 mL). The mixture was heated to 50° C. for 30 min., then the organic solvents were evaporated. The residue was diluted with $H_2O$ (4 mL) and centrifuged. The supernatant was decanted and the insoluble lithium salt was suspended in $H_2O$ (4 mL). The mixture was acidified with 1N aq HCl, stirred vigorously and filtered to afford the title compound as a light yellow solid; m.p. 159°–162° C.

EXAMPLE 2

3-[5-(4-Chlorobenzyl)-2-methyl-8-(5-phenylpyridin-2-ylmethoxy)-3,5-dihydro-3-oxo-2H-thiopyrano[4,3,2-cd]indol-4-yl]-2,2-dimethylpropanoic acid Step 1: Methyl 3-[1-(4-chlorobenzyl)-3-t-butylthio-5-methoxyindol-2-yl]-2,2-dimethylpropanoate To a solution of 39 g methyl 5-t-butylthio-2,2-dimethyl-4-oxopentanoate (Ketone 2) in a mixture of toluene (300 mL) and HOAc (150 mL) was added NaOAc (15 g) and 1-(4-methoxyphenyl)-1-(4-chlorobenzyl)-hydrazine hydrochloride (50 g). The reaction was stirred at r.t. for 3 days under argon in the dark. The mixture was poured onto $H_2O$ (1 L) and extracted with 3× EtOAc (500 mL). The EtOAc was washed with 3× $H_2O$ (500 mL) then once with $NaHCO_3$ solution. The organic phase was dried ($MgSO_4$), evaporated to dryness, and the residue crystallised from $Et_2O$/hexane 2:1 to afford the title compound; m.p. 102°–103° C.

Step 2: Methyl 3-[1-(4-chlorobenzyl)-5-methoxyindol-2-yl]-2,2-dimethylpropanoate A mixture of the product from Step 1 (2.03 g, 4.29 mmol) and thiosalicylic acid (1.32 g, 8.58 mmol) in TFA (25 mL) was refluxed for 2.5 hours. The TFA was evaporated, the residue was diluted with EtOAc, washed twice with 1N aq NaOH, then 3× with $H_2O$, dried and evaporated to afford the crude title product as a thick oil which was taken as such into the next step.

Step 3: Methyl 3-[3-(α-carbomethoxyethyl-thio)-1-(4-chlorobenzyl)-5-methoxyindol-2-yl]-2,2-dimethyl propanoate To a solution of bis(α-carbomethoxyethyl)disulfide (714 mg, 3 mmol) in 1,2-dichloroethane (10 mL) there was added $SO_2Cl_2$ (378 mg, 2.8 mmol) and the resulting solution was stirred at r.t. for 20 min. It was then added slowly to a cooled (0° C.) solution of the crude product from Step 2 (1.8 g, 4.6 mmol) in DMF (15 mL). Stirring was continued at 0° C. for 1.5 hours, then $H_2O$ (50 mL) was added and the mixture was extracted with $CH_2Cl_2$. The crude product thus obtained was chromatographed on silica gel, eluting with a 1:5 mixture of EtOAc and hexane to afford the title compound as a thick oil.

Step 4: Methyl 3-[3-(α-carboxyethylthio)-(1-(4-chlorobenzyl)-5-methoxyindol-2-yl]-2,2-dimethyl-propanoate To a solution of diester from Step 2 (1.5 g) in MeOH (25 mL) there was added 1M aq LiOH (12 mL) and the mixture was stirred at r.t. for 2 hours. The mixture was diluted with $H_2O$, acidified with 1N HCl and the precipitate filtered to afford the crude product as a white solid which was used as such in the next step.

Step 5: Methyl 3-[5-(4-chlorobenzyl)-8-methoxy-2-methyl-3,5-dihydro-3-oxo-2H-thiopyrano[4,3,2-cd]indol-4-yl]-2,2-dimethylpropanoate To a suspension of the crude product from Step 4 (747 mg, 1.52 mmol) in $CH_2Cl_2$ (15 mL) there was added oxalyl chloride (291 mg, 2.29 mmol) and DMF (10 μL). The mixture was stirred at r.t. for 30 min., then there was added $AlCl_3$, 1.9M in nitrobenzene (3.2 mL, 6.1 mmol), and stirring was continued at r.t. for 1 hour. Iced $H_2O$ was added and the mixture was extracted 4× with $CH_2Cl_2$. The crude product thus obtained was chromatographed on silica gel, eluting with a 1:3 mixture of EtOAc and hexane, to afford the title compound as a thick oil.

Step 6: Methyl 3-[5-(4-chlorobenzyl-8-hydroxy-2-methyl-3,5-dihydro-3-oxo-2H-thiopyrano[4,3,2-cd]indol-4-yl]-2,2-dimethylpropanoate To a suspension of 97% NaH (51 mg, 2.12 mmol) in DMF (6 mL) and DMPU (0.6 mL) at 0° C. there was added 2-methyl-2-propanethiol (238 mg, 2.65 mmol) and the mixture was stirred at 0° C. for 30 min. To this mixture there was added a solution of product from Step 5 (250 mg, 0.53 mmol) in DMF (2 mL). The mixture was then heated at 140° C. for 1 hour, cooled, diluted with $H_2O$, acidified with 1N HCl and extracted twice with $Et_2O$. The product thus obtained was esterified with ethereal diazomethane at r.t., and chromatographed on silica gel, eluting with a 1:2 mixture of EtOAc and hexane to afford the title compound as a thick oil.

Step 7: Methyl 3-[5-(4-chlorobenzyl)-2-methyl-8-(5-phenylpyridin-2-ylmethoxy)-3,5-dihydro-3-oxo-2H-thiopyrano[4,3,2-cd]indol-4-yl]-2,2-dimethyl propanoate Following the procedure described in Example 1, Step 7, but substituting the product from Step 6 for 5-(4-chlorobenzyl)-8-hydroxy-4-(2-hydroxyethyl)-2-methyl-3,5-dihydro-2H-thiopyrano[4,3,2-cd]indole, the desired product was obtained as a thick oil Step 8: 3-[5-(4-Chlorobenzyl)-2-methyl-8-(5-phenyl-pyridin-2-ylmethoxy)-3,5-dihydro-3-oxo-2H-thiopyrano[4,3,2-cd]indol-4-yl]-2,2-dimethylpropanoic acid To a solution of the product from Step 7 (40 mg) in THF (1 mL) and MeOH (1 mL) there was added 2.5 N aq NaOH (1 mL) and the mixture was refluxed for 3.5 hours. The organic solvents were evaporated, the residue was diluted with H₂O, acidified with 1N HCl and filtered to afford the title compound as a yellow solid; m.p. 168° (dec).

What is claimed is:

1. A compound of the formula:

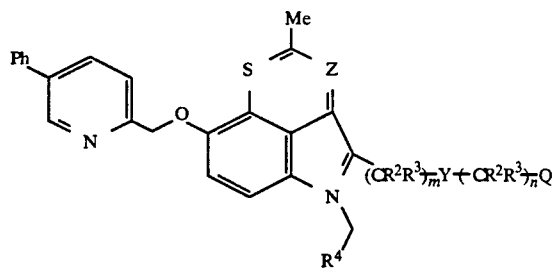

wherein:
$R^2$ is H, $C_1$-$C_7$ lower alkyl, hydroxy, or $C_1$-$C_7$ lower alkoxy, or two $R^2$ groups on adjacent carbon atoms may be a bond;
$R^3$ is H or lower alkyl;
m is 0 to 3;
n is 0 to 3;
$R^4$ is [phenyl($R^{10}$)2]t;
$R^{10}$ is H, $C_1$-$C_7$ lower alkyl, or halogen;
t is 1 or 2;
Y is a bond, O or S;
Q is —$CO_2H$ or —$CONHS(O)_2R^{12}$;
$R^{12}$ is $C_1$-$C_7$ lower alkyl, $R^{10}$-phenyl, $CF_3$, $NH_2$ or $N(C_1$-$C_7$ lower alkyl)$_2$;
Z is $CHR^{20}$, $CHWR^6$, or CO;
$R^6$ is H or $C_1$-$C_7$ lower alkyl;
$R^{20}$ is H or $C_1$-$C_7$ lower alkyl;
W is O, S, or $NR^6$;
or a pharmaceutically acceptable salt thereof.

2. A compound of claim 1 wherein the substituents are:

| Ex | $R^4$ | Z | $(CR^2R^3)m$ | Y | $(CR^2R^3)n$ | Q |
|---|---|---|---|---|---|---|
| 1. | 4-Cl—Ph | $CH_2$ | $CH_2CH_2$ | O | CH(Et) | $CO_2H$ |
| 2. | 4-Cl—Ph | CO | — | — | $CH_2C(Me)_2$ | $CO_2H$ |
| 6. | 3-F—Ph | $CH_2$ | — | — | $CH_2C(Me)_2$ | $CO_2H$ |

3. A method of treating asthma in a mammal comprising administering to a mammal in need of such treatment a therapeutically effective amount of a compound of claim 1.

* * * * *